United States Patent
Temple

(10) Patent No.: US 9,848,762 B2
(45) Date of Patent: Dec. 26, 2017

(54) HEATER FOR SURGICAL VIEWING INSTRUMENTS

(76) Inventor: John Temple, Chelsea, MI (US)

(*) Notice: Subject to any disclaimer, the term of this patent is extended or adjusted under 35 U.S.C. 154(b) by 2245 days.

(21) Appl. No.: 12/471,895

(22) Filed: May 26, 2009

(65) Prior Publication Data

US 2009/0247832 A1    Oct. 1, 2009

Related U.S. Application Data

(63) Continuation-in-part of application No. 10/827,493, filed on Apr. 19, 2004, now Pat. No. 7,537,563.

(60) Provisional application No. 60/463,642, filed on Apr. 17, 2003.

(51) Int. Cl.
   *A61B 1/06*    (2006.01)
   *A61B 1/12*    (2006.01)
   *A61B 50/00*    (2016.01)

(52) U.S. Cl.
   CPC .............. *A61B 1/128* (2013.01); *A61B 1/127* (2013.01); *A61B 50/00* (2016.02); *A61B 2050/0017* (2016.02)

(58) Field of Classification Search
   USPC ................................................. 600/169, 133
   See application file for complete search history.

(56) References Cited

U.S. PATENT DOCUMENTS

| | | | |
|---|---|---|---|
| 3,463,161 A * | 8/1969 | Andrassy ...................... 607/110 |
| 4,077,390 A * | 3/1978 | Stanley et al. ............ 126/263.04 |
| 5,205,278 A * | 4/1993 | Wang ........................ 126/263.03 |
| 5,295,964 A * | 3/1994 | Gauthier ....................... 604/113 |
| 5,351,675 A | 10/1994 | Brodsky |
| 5,549,543 A | 8/1996 | Kim |
| 5,651,757 A | 7/1997 | Meckstroth |
| 5,805,766 A * | 9/1998 | Wang ............................ 392/343 |
| 5,910,106 A | 6/1999 | Morgan et al. |
| 6,234,635 B1 | 5/2001 | Seitzinger et al. |
| 2002/0022762 A1 | 2/2002 | Beane et al. |
| 2002/0157682 A1* | 10/2002 | Ueyama et al. .............. 132/221 |
| 2008/0145644 A1* | 6/2008 | Amundson et al. ....... 428/321.1 |

* cited by examiner

*Primary Examiner* — Matthew J Kasztejna
(74) *Attorney, Agent, or Firm* — John G. Posa; Belzer PC

(57) ABSTRACT

A system and associated method is used for warming an endoscope, laparoscope, or other such instrument to minimize fogging. A flexible pad has a length, a width and a periphery for wrapping around the instrument and a plurality of separate chambers defined through partitions. Each of the separate chambers includes an activation disc and a mixture of water and sodium acetate to generate heat through an exothermic reaction initiated through manual manipulation of the disc for that chamber. The pad is preferably made from two plastic sheets of substantially equal size, with the chambers being formed by heat-sealing or otherwise bonding the periphery of the sheets and the partitions. At least some of the partitions establish lengthwise and/or widthwise fold lines in the pad. At least one of the partitions may include a gap to facilitate fluid transfer of the mixture. The disc is preferably made of perforated stainless steel. A housing may be provided to contain the pad in sleeve form, and an optional heat-conductive tube may be used to receive the instrument around which the pad is wrapped.

2 Claims, 6 Drawing Sheets

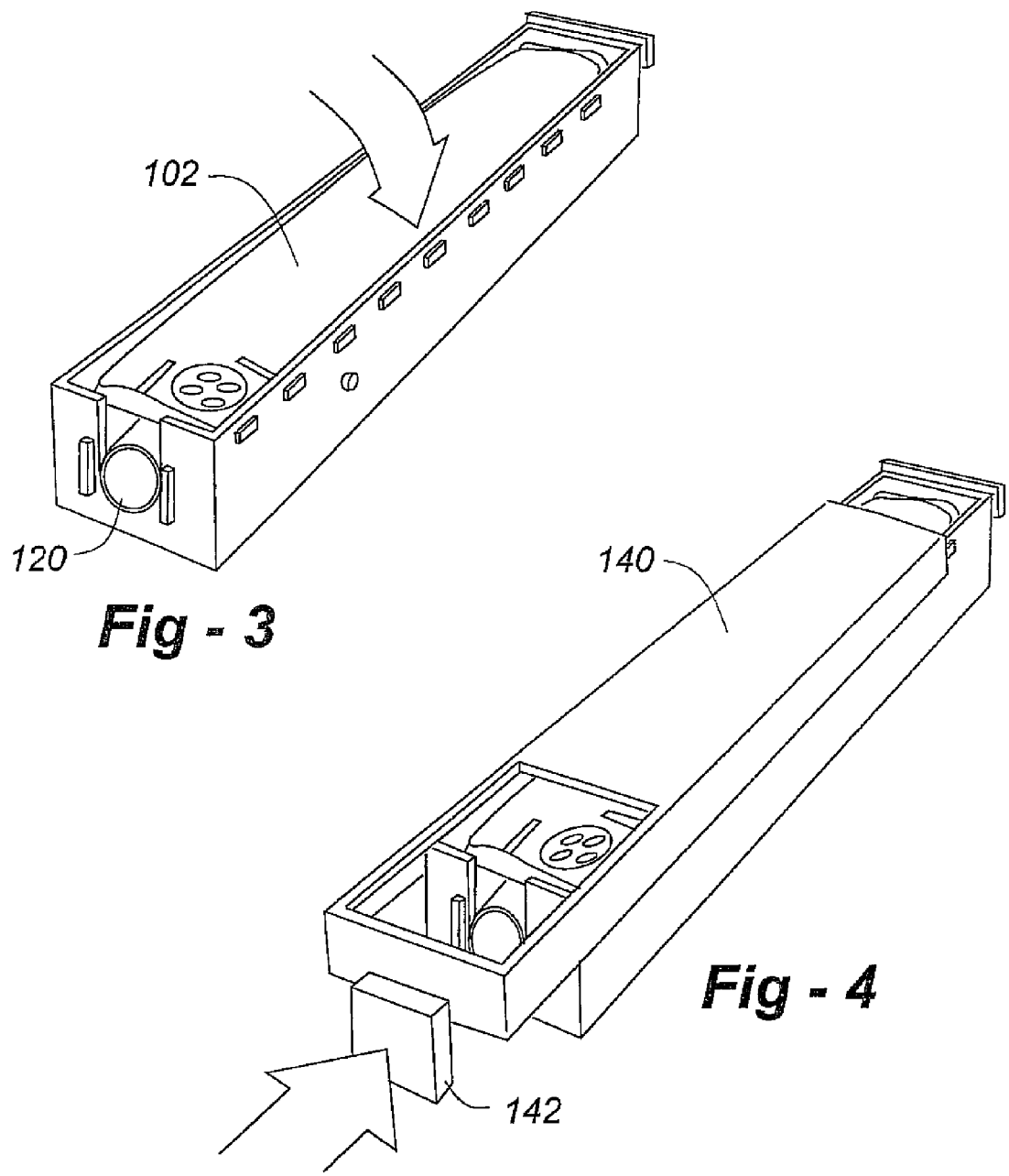

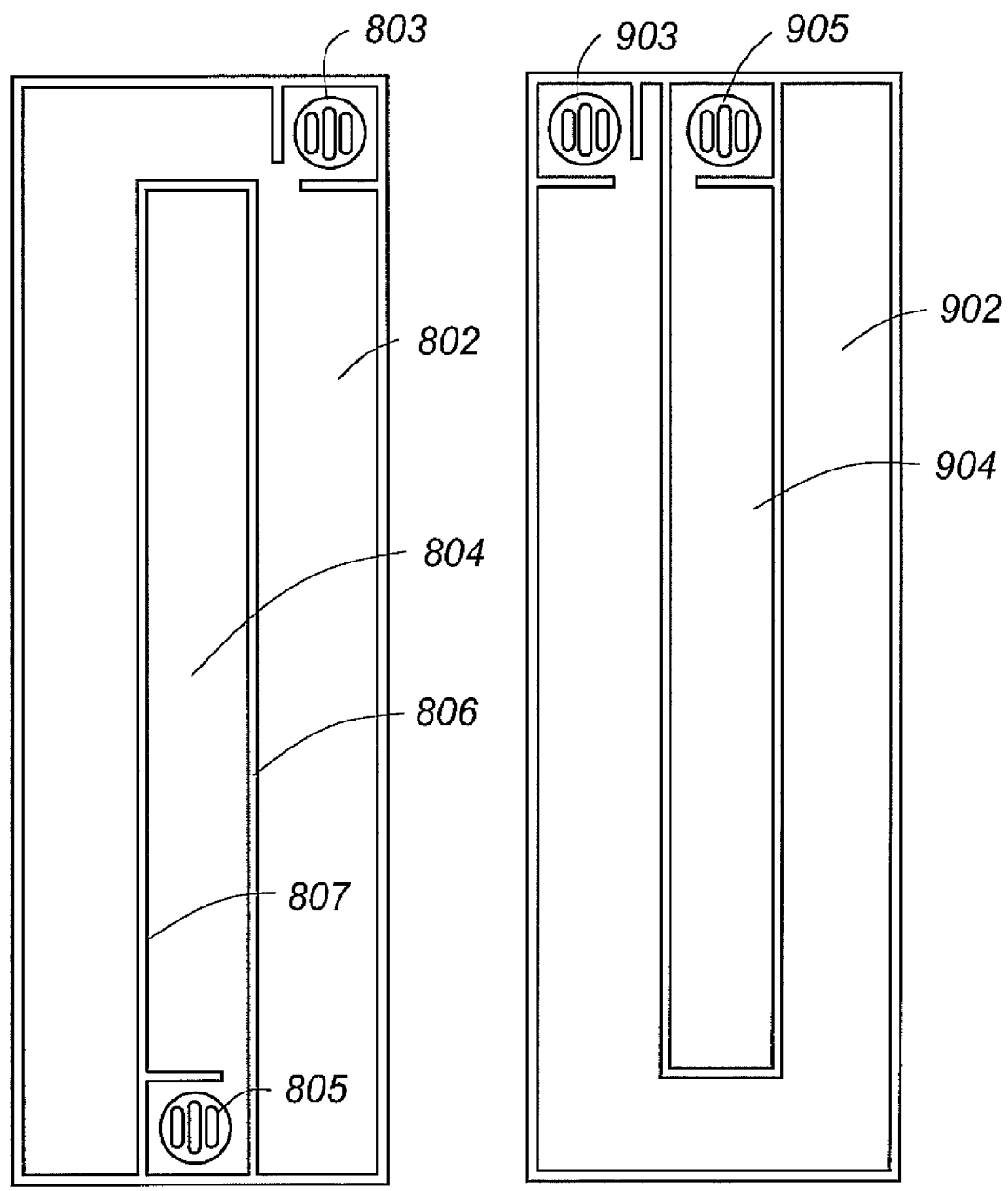

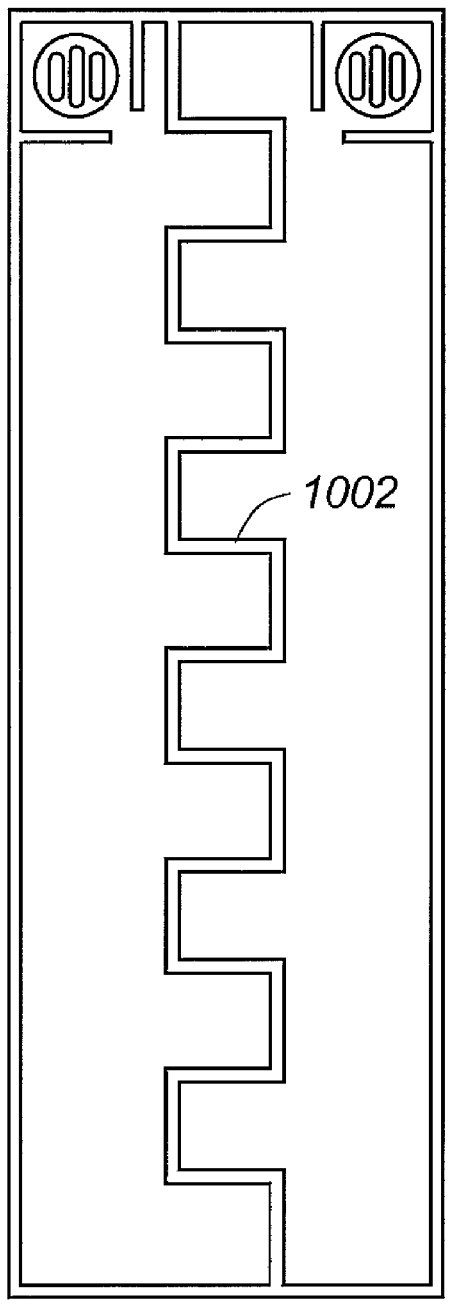 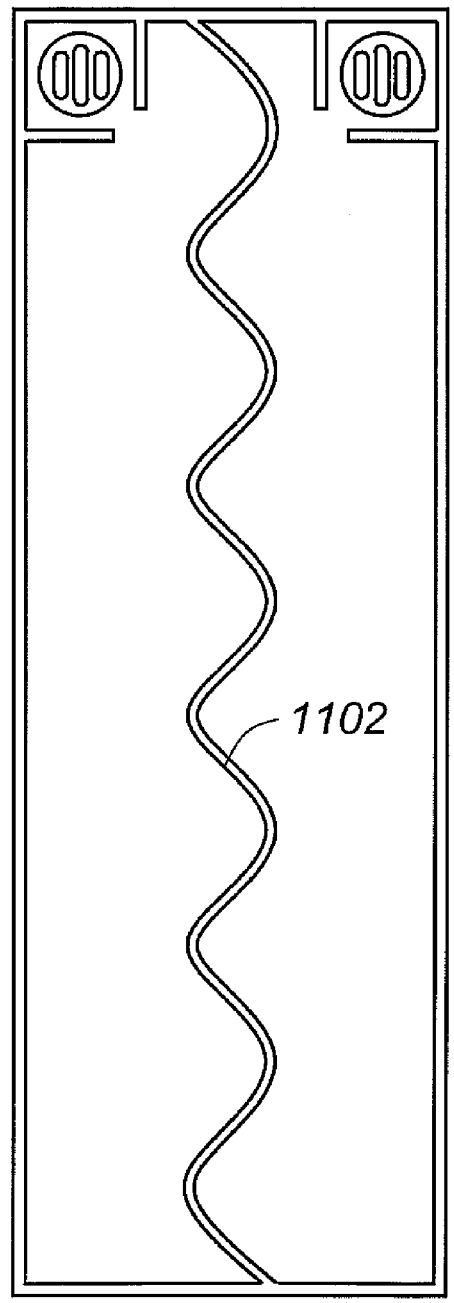
*Fig - 10*   *Fig - 11*

HEATER FOR SURGICAL VIEWING INSTRUMENTS

REFERENCE TO RELATED APPLICATIONS

This application is a continuation-in-part of U.S. patent application Ser. No. 10/827,493, filed Apr. 17, 2003, which claims priority from U.S. Provisional Patent Application Ser. No. 60/463,642, filed Apr. 17, 2003, the entire content of each application is incorporated herein by reference.

FIELD OF THE INVENTION

This invention relates generally to surgical instruments and supplies and, in particular, to heater for medical and surgical viewers subject to fogging.

BACKGROUND OF THE INVENTION

In minimally invasive surgical (MIS) procedures, elongated illuminators and viewers, i.e., laparoscopes and endoscopes, are inserted through small incisions in the abdominal wall or elsewhere. The viewer is typically coupled to a video camera that shows the operating field on a monitor.

A common problem is that the lens on the viewer becomes fogged. When the viewer is inserted, the lens is typically at operating room temperature which is often much colder than room temperature. The body cavity is at body temperature and high humidity. As such, water droplets condense on the lens, obscuring the view. When the lens fogs, the surgeon must remove the instrument, clean the lens, and reinsert the instrument at which time fogging often begins again.

To address this problem, the instrument may be immersed in a warm saline bath before surgery and during cleaning. This can be time-consuming and it is difficult to control temperature to consistent, effective working temperature.

An automated approach is described in Published U.S. Patent Application 2002/0022762 A1. A lens warming and cleaning device for use with an optical surgical instrument is disclosed. The device includes a heat-conducting tube sized and shaped to receive the lens portion of the instrument, a heating element thermally coupled to an exterior of the tube, and a cleaning member disposed within the tube. The cleaning member is disposed such that when the lens portion of the instrument is inserted into the tube, the lens portion contacts the cleaning member.

The heating element comprises a flexible pad that surrounds at least a portion of the tube including the lens portion. The pad may be wrapped around tube or attached to tube using an adhesive or hook-and-loop fasteners.

In one disclosed embodiment, the heating pad includes a flexible, air-permeable outer bag that encases a chemical mixture that generates an exothermic reaction when activated. The chemical mixture can be, e.g., a mixture of iron powder, water, cellulose, vermiculite, activated carbon, and salt. Exposing the mixture to atmospheric oxygen triggers an exothermic reaction that warms the pad to a temperature of about 60° C. and sustains that temperature for about six hours.

Other types of known exothermic reaction mixtures can be used. For example, the mixture can consist of iron powder, a chloride or sulfate of a metal having a tendency of ionization greater than iron, active carbon, and water. Alternatively, the chemical mixture can be a super-cooled, supersaturated aqueous solution of sodium acetate. The pad can also employ other types of exothermic chemical reactions to generate heat, or it can include a resistance heater powered by, e.g., a battery or an external source of electricity.

The problems with this system are two-fold. First, the addition of a cleaning mechanism is all embodiments constitutes an unnecessary complication, since warming is by far the greatest need. Additionally, although "other types of exothermic chemical reactions" are mentioned in passing, activation methods and apparatus are not disclosed. Accordingly, the need remains for a less expensive yet effective endoscope/laparoscope warming system.

SUMMARY OF THE INVENTION

This invention resides in a system and associated method for warming an endoscope, laparoscope, or other such instrument to minimize fogging. The preferred embodiment comprises a flexible pad having a length, a width and a periphery for wrapping around the instrument and a plurality of separate chambers defined through partitions. Each of the separate chambers includes an activation disc and a mixture of water and sodium acetate to generate heat through an exothermic reaction initiated through manual manipulation of the disc for that chamber.

The pad is preferably made from two plastic sheets of substantially equal size, with the chambers being formed by heat-sealing or otherwise bonding the periphery of the sheets and the partitions. At least some of the partitions establish lengthwise and/or widthwise fold lines in the pad. At least one of the partitions may include a gap to facilitate fluid transfer of the mixture. In the preferred embodiments, the disc is made of perforated stainless steel. A housing may be provided to contain the pad in sleeve form, and an optional heat-conductive tube may be used to receive the instrument around which the pad is wrapped.

BRIEF DESCRIPTION OF THE DRAWINGS

FIG. 3 is a drawing which shows how the pad is then folded over on top of the tube to completely surround it;

FIG. 4 illustrates the addition of the top cover without a hinge lid;

FIG. 8 is a drawing that depicts an alternative embodiment of the invention having a plurality of heatable chambers;

FIG. 9 depicts an alternative embodiment of the invention having a plurality of heatable chambers and activation discs at the same end;

FIG. 10 shows an alternative embodiment of the invention having a plurality of heatable chambers in a different arrangement;

FIG. 11 shows an alternative embodiment of the invention having a plurality of heatable chambers in yet a further arrangement;

DETAILED DESCRIPTION OF THE INVENTION

This invention improves upon the prior art by providing a low-cost yet effective heater for medical/surgical viewers subject to fogging, including endoscopes, laparoscopes, elongated microscopes, and so forth. Broadly, the apparatus includes a housing into which there is disposed a heating pad containing chemicals to produce heat through an exothermic reaction. The pad is rolled in the housing to create an elongated cavity in alignment with an aperture through the housing into which the instrument to be warmed is placed. In a preferred embodiment, a heat-conductive tube is also included between the rolled pad and instrument to provide for more consistent heating, and silicon acetate is used as the active ingredient in the pad, generated heat through contact with water also in the pad.

Figure 1:
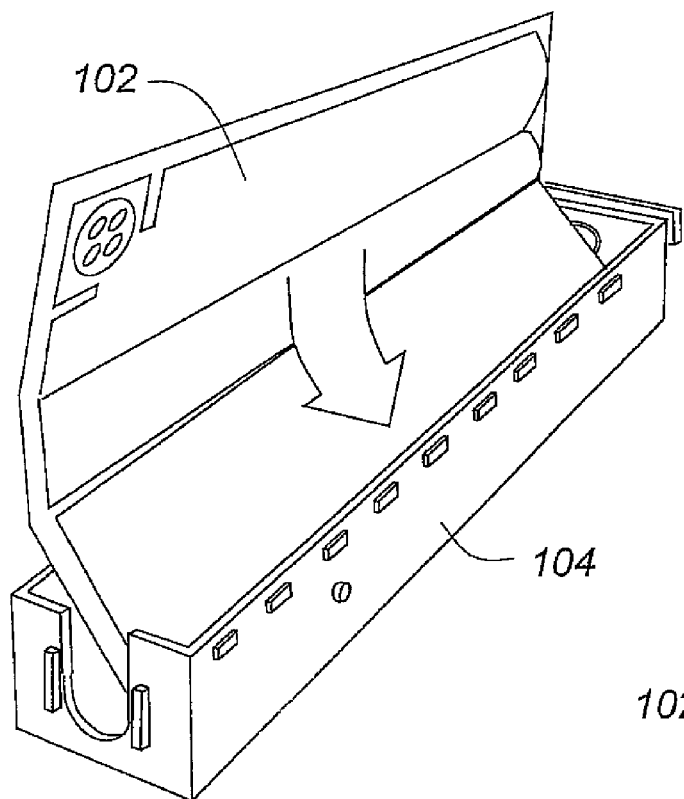
FIG. 1 is a drawing which shows the way in which a heating pad is inserted into a housing with the top cover removed.
Figure 2:
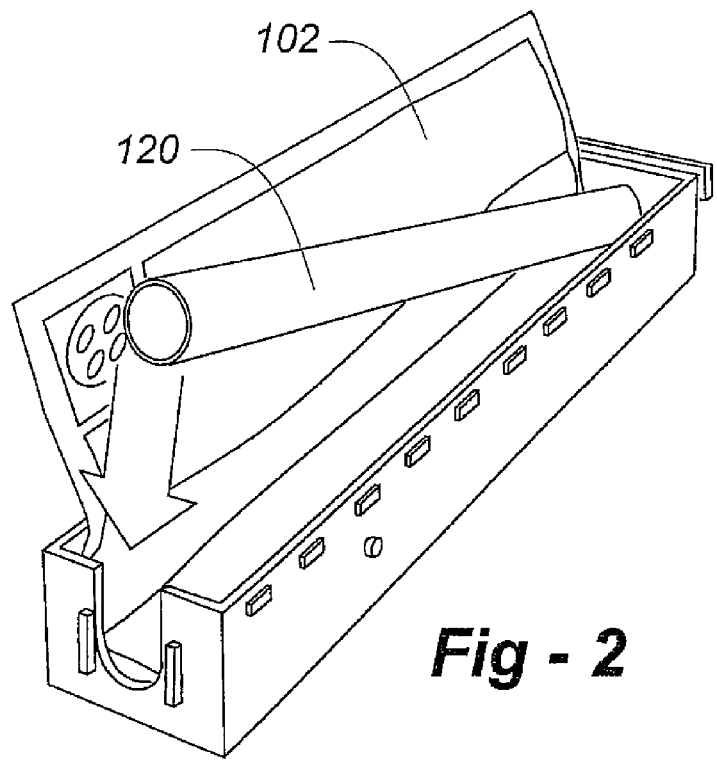
FIG. 2 shows the way in which an internal tube is placed into the pad.

Now making reference to the drawings, FIG. 1 is an oblique representation showing the way in which pad 102 is placed into a housing 104 without a lid or hinged access panel, which will be described with reference to subsequent figures. In FIG. 2, a heat-conductive tube 120 of aluminum, stainless steel, or other suitable metal or material is placed into the partially rolled pad 102.

Figure 5:
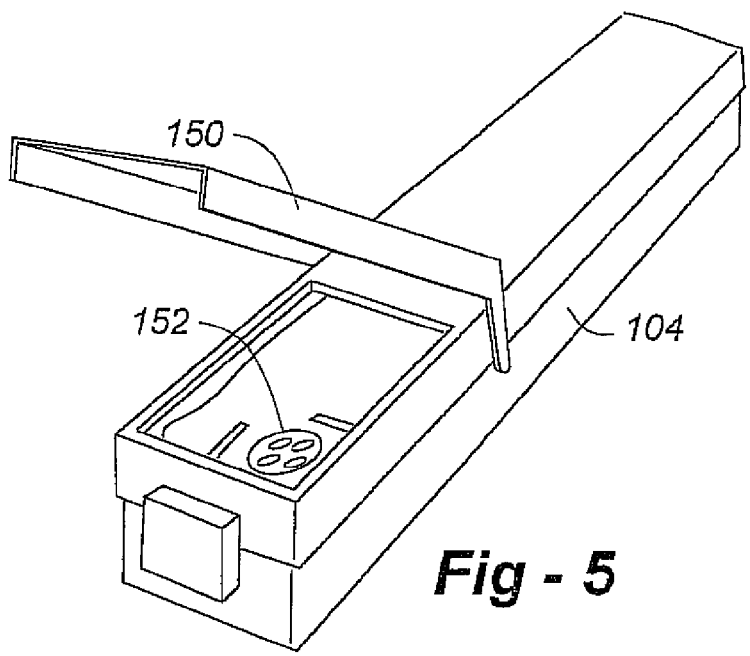
FIG. 5 is the drawing of a completed unit including a hinge lid.

In FIG. 3, the remaining portion of the pad 102 is folded over and onto the tube 120, again, without the lid or access panel being shown. In FIG. 4, the lid 140 is placed onto the housing, with an access door 142 being provided in alignment with the opening of tube 120, as shown. In FIG. 5, a hinged lid 150 is added, allowing a user to open the lid to gain access to an activation area 152 on the pad, which will be described in further detail below.

Figure 6:
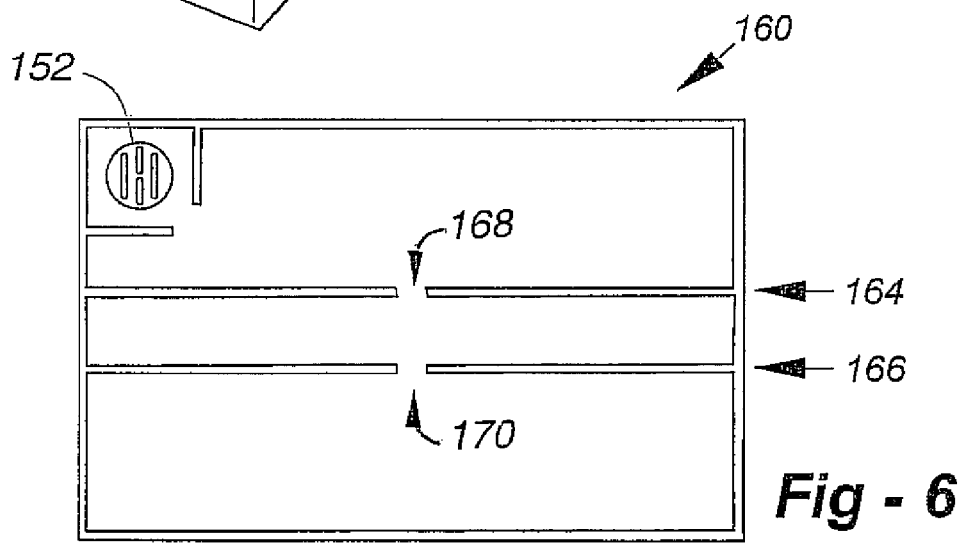
FIG. 6 is a drawing of the preferred embodiment the pad.

FIG. 6 is a plan view of a preferred heating pad 160 according to the invention. The pad contains a mixture of sodium acetate and water, and, unique to the invention, a particular spot 152 is provided, including a stainless steel disc to initiate the chemical reaction. Referring back to FIG. 5, this disc is placed on the pad so that when rolled into the housing, the area 152 is easily accessible when the hinged lid 150 is opened. Note that the pad 160 is also otherwise partitioned along lines 164 and 166 to conveniently provide fold areas for easier placement into the housing 104.

Figure 7:
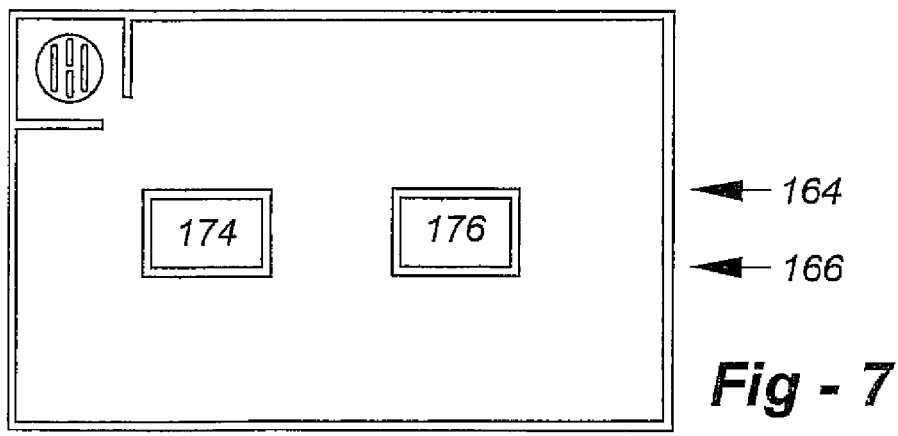
FIG. 7 is a drawing illustrating an alternative embodiment of a pad.

FIG. 7 illustrates an alternative design for the pad, wherein, instead of elongated seams 164 and 166, islands 174 and 176 are provided instead, these also being conducive to folding along the same desired line.

FIG. 8 is a drawing that depicts an alternative embodiment of the invention having a plurality of heatable chambers 802, 804 separated by sealed segments such as 806. Although two separate chambers are shown, more may be accommodated with appropriate seals. The activation disc for chamber 802 is shown at 803, whereas the disc for chamber 804 is shown at 805. The advantage of separate heatable chambers is that one chamber may be heated and used during a particular procedure and, if the procedure is sufficiently long, a different chamber may be heated for prolonged use. Note that in this and the embodiments which follow, sealed partitions such as 806, 807 may, or may not, double for use as fold lines. FIG. 9 depicts an alternative embodiment of the invention having a plurality of heatable chambers 902, 904 and activation discs 903, 905 at the same end;

FIG. 10 shows an alternative embodiment of the invention having a plurality of heatable chambers in a different arrangement, separated here with a meandering partition composed of straight segments. FIG. 11 shows an alternative embodiment of the invention having a plurality of heatable chambers in yet a further arrangement separated with a wavy partition 1102.

Figure 12:
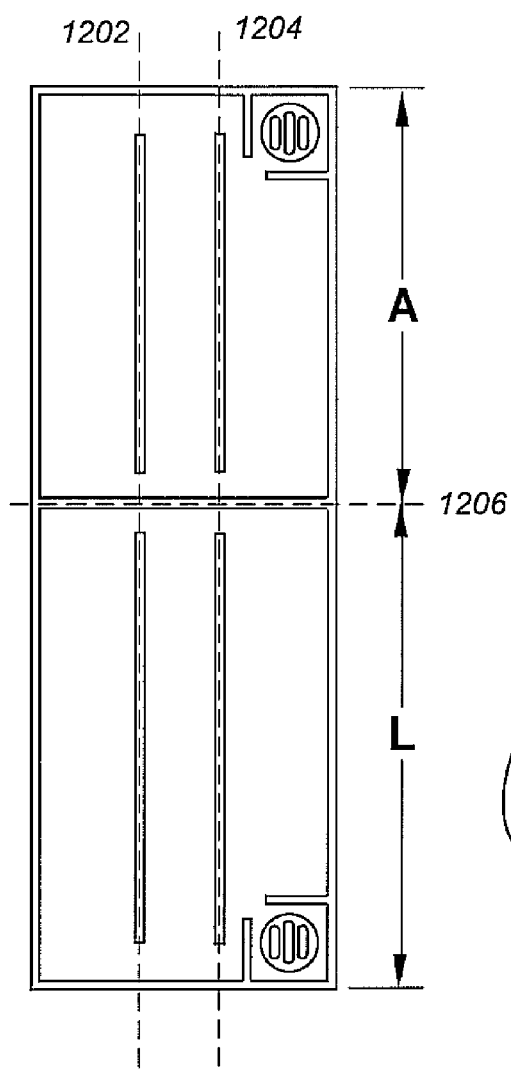
FIG. 12 shows an alternative embodiment of the invention having a plurality of heatable chambers with common fold lines.
Figure 13:
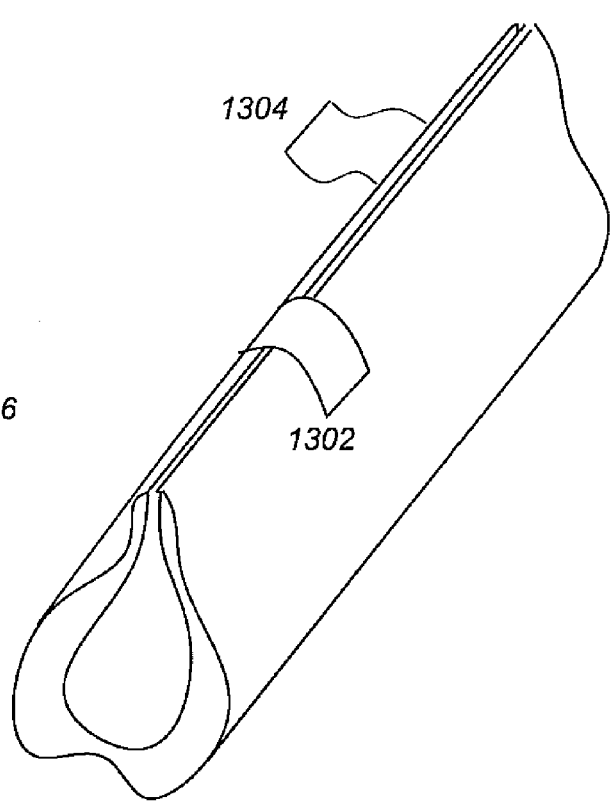
FIG. 13 shows how one or more pieces of tape or other elements may be used to secure one edge of the pad to another once the pad is wrapped around an instrument to be warmed.

FIG. 12 shows an alternative embodiment of the invention having a plurality of heatable chambers with common fold lines 1202, 1204. A transverse fold line 1206 is also shown enabling the pad to form a pocket-like structure. The distances A and L may be the same of different. In all embodiments disclosed herein, the structure may be folded lengthwise (or widthwise in the case of FIG. 12), and secured with one or more pieces of tape 1302, 1304 or other fasteners such as hook-and-loop tabs, etc., as shown in FIG. 13.

I claim:

1. An article for warming an endoscope, laparoscope, or other elongated instrument to minimize fogging, consisting of:
    a flexible pad configured to wrap around the instrument, the pad having a length, a width and a periphery;
    wherein the pad is formed by heat-sealing or otherwise bonding together two plastic sheets of substantially equal size, including a peripheral bond providing a seal around the two sheets, a lengthwise bond dividing the pad into two separate chambers, and one or more partial bonds within each chamber with gaps that facilitate fluid transfer of the mixture within each respective chamber but not between the chambers;
    wherein the lengthwise bond is shared by the two separate chambers and further provides a lengthwise fold line to facilitate the wrapping of the pad around an instrument;
    each of the separate chambers including an activation disc and a mixture of water and sodium acetate to generate heat through an exothermic reaction initiated through manual manipulation of the disc for that chamber; and
    one or more pieces of tape or other fasteners to secure one edge of the pad to another once wrapped around an instrument to be warmed.

2. The article of claim 1, wherein each activation disc is made of perforated stainless steel.

* * * * *